(12) United States Patent
Xu

(10) Patent No.: US 9,856,215 B2
(45) Date of Patent: Jan. 2, 2018

(54) PREPARATION METHOD OF NINTEDANIB

(71) Applicant: SUZHOU MIRACPHARMA TECHNOLOGY CO., LTD., Suzhou (CN)

(72) Inventor: Xuenong Xu, Suzhou (CN)

(73) Assignee: SUZHOU MIRAPHARMA TECHNOLOGY CO., LTD., Suzhou (CN)

( * ) Notice: Subject to any disclaimer, the term of this patent is extended or adjusted under 35 U.S.C. 154(b) by 0 days.

(21) Appl. No.: 15/453,892

(22) Filed: Mar. 8, 2017

(65) Prior Publication Data

US 2017/0174625 A1    Jun. 22, 2017

Related U.S. Application Data

(63) Continuation of application No. PCT/CN2015/085719, filed on Jul. 31, 2015.

(30) Foreign Application Priority Data

Sep. 9, 2014   (CN) .......................... 2014 1 0455826

(51) Int. Cl.
*C07D 209/34*   (2006.01)

(52) U.S. Cl.
CPC .................................. *C07D 209/34* (2013.01)

(58) Field of Classification Search
None
See application file for complete search history.

(56) References Cited

FOREIGN PATENT DOCUMENTS

| CN | 101883756 A | 11/2010 |
|---|---|---|
| CN | 104262232 A | 1/2015 |
| WO | 2012068441 A2 | 5/2012 |

OTHER PUBLICATIONS

Machine translation for CN104262232A, Jan. 7, 2015, 9 pages.*

* cited by examiner

*Primary Examiner* — Emily Bernhardt
(74) *Attorney, Agent, or Firm* — Perkins Coie LLP

(57) ABSTRACT

Disclosed is a preparation method of nintedanib (I), comprising the following steps: carrying out a condensation reaction on 4-(R acetate-2-yl)-3-nitrobenzoate (II) and trimethyl orthobenzoate to obtain (E)-4-[(2-methoxybenzylidene) R acetate-2-yl]-3-nitrobenzoate (III); carrying out a substitution reaction on the compound (EI) and N-(4-aminophenyl)-N-methyl-2-(4-methyl piperazine-1-yl) acetamide (IV) under the action of an acid-binding agent to generate (Z)-4-{[2-(N-methyl-2-(4-methyl piperazine-1-yl) acetamido-aniline) benzylidene] R acetate-2-yl}-3-nitrobenzoate (V); and sequentially carrying out reduction reactions and cyc-lization reactions on the compound (V) to prepare the nintedanib (I). The preparation method has an easily obtained raw material and a simple process, is economical and environmentally friendly, and is suitable for industrial production.

9 Claims, No Drawings

PREPARATION METHOD OF NINTEDANIB

CROSS REFERENCE TO RELATED APPLICATIONS

This application is a continuation of PCT NO. PCT/CN2015/085719 filed Jul. 31, 2015, which claims priority to CN 201410455826.7 filed Sep. 9, 2014, both of which are incorporated by reference.

TECHNICAL FIELD

The present invention relates to the organic synthetic route design and the technical field for APIs and intermediates preparation, especially relating to the preparation method of Nintedaib for the treatment of idiopathic pulmonary fibrosis.

BACKGROUND

Nintedanib developed by Boehringer Ingelheim is a kind of oral triple angiokinase inhibitor which can simultaneously block three growth factor receptors: the endothelial growth factor receptor, the platelet-derived growth factor receptor and the fibroblast growth factor receptor. The blockade of these receptors may lead to inhibition of angiogenesis, which plays a key role in inhibiting tumor growth. The drug used for the treatment of idiopathic pulmonary fibrosis was granted the title of "breakthrough therapy drug" by U.S. FDA for the first time in July 2014, and the trade name of its ethane sulfonate preparation is Vargatef.

The chemical name of Nintedanib: (Z)-{1-[4-(N-((4-methyl-piperazin-1-yl)-methylcarbonyl)-N-methyl-amino)phenylamino]-1-phenyl-methyl}-2-oxo-2,3-dihydro-1H-indole-6-carboxylate (I); the structural formula as follows:

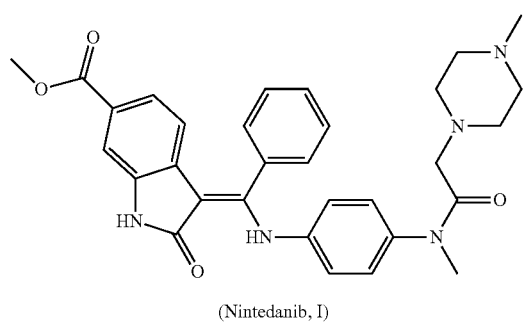

(Nintedanib, I)

The preparation method of Nintedanib has been reported, and the synthesis method of Nintedanib and its analogue has been reported in PCT patents WO2001027081 and WO2009071523 from the original company. In this method, the drug is generated through condensation reaction of two key intermediates A and B under the alkaline condition.

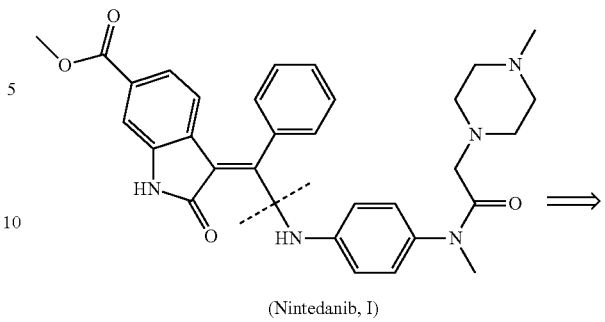

(Nintedanib, I)

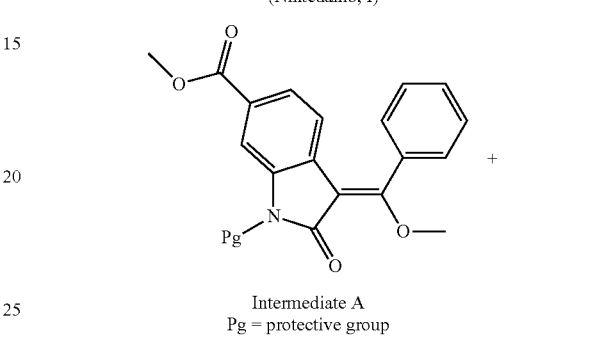

Intermediate A
Pg = protective group

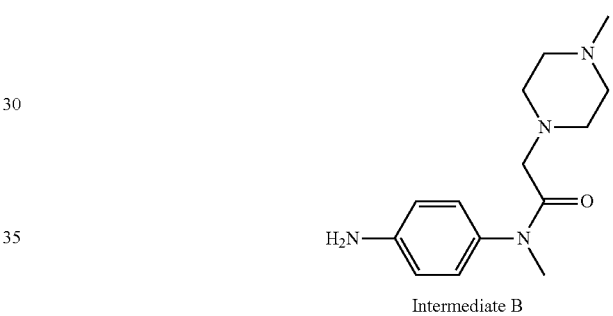

Intermediate B

Additionally, the synthesis method of intermediates A and B are further reported in the literature J. Med. Chem, Pages 4466-4480, Vol. 52, 2009 and Chinese Journal of Pharmaceuticals, Pages 726-729, Vol. 43, Issue 9, 2012. And based on the optimized reaction condition, reaction sequence, rate of charge and catalyst selection, the synthetic route stated above becomes more simple and reasonable.

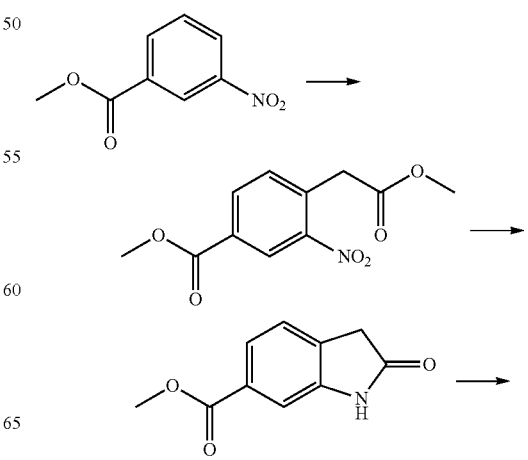

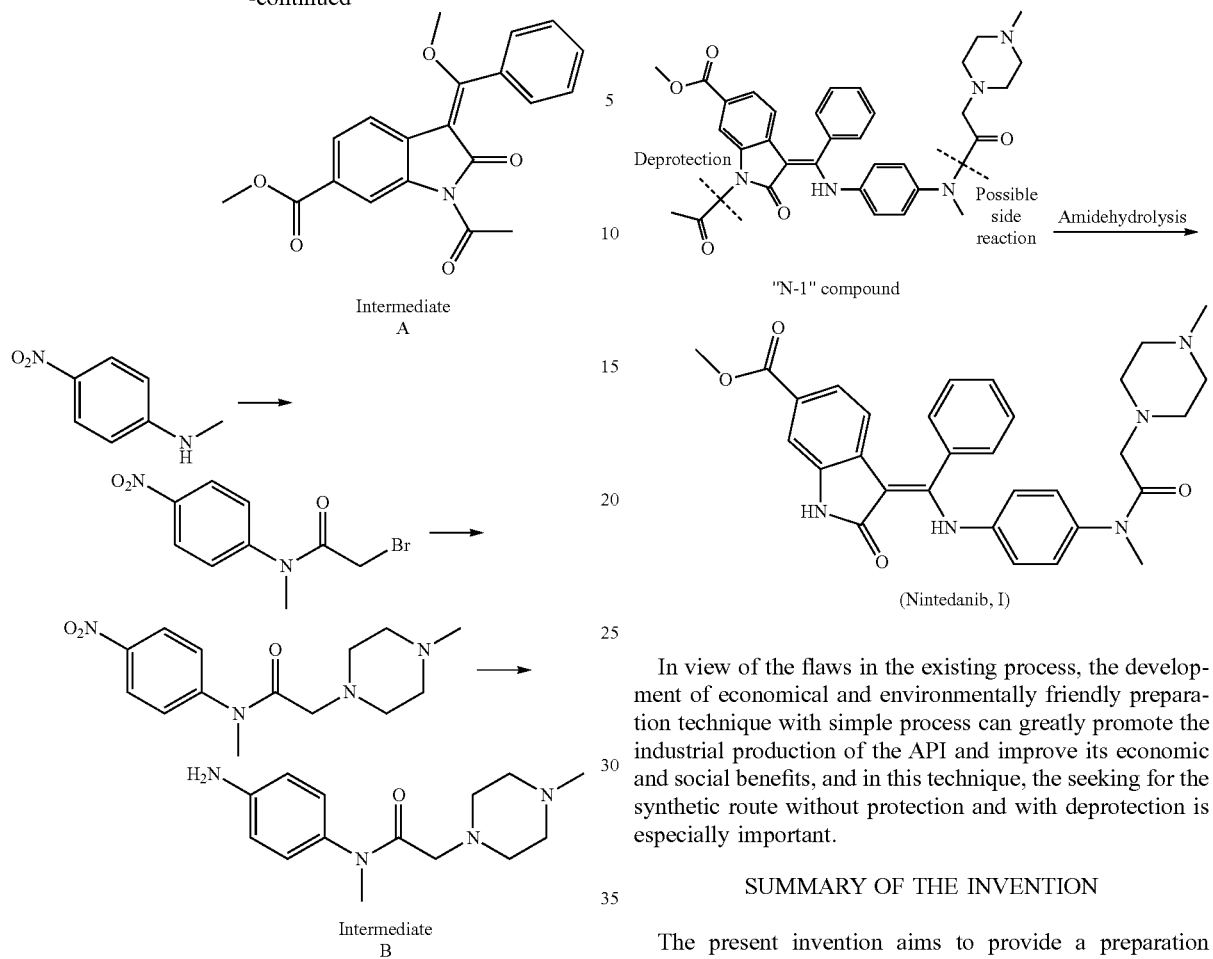

Intermediate A

Intermediate B

By analyzing the structural characteristics of Nintedanib and combination of the current synthesis method of this compound and its intermediates, the applicant finds cis "methylene on indoline ring" structure and its formation method is the key to the whole synthesis process. It is also one of the difficulties. The process from the original company is that through the 3-position substitution and condensation reactions on 2-oxo-indoline ring and trimethyl orthobenzoate under the action of acetic anhydride, the trans "methylene" derivative, namely intermediate A is obtained. The methoxy in intermediate A is used as the leaving group to get a substitution reaction with the anilino in intermediate B, thus generating the target product. The intramolecular hydrogen bond in intermediate A can promote the transformation from "trans" to "cis".

However, there exist some flaws or weaknesses in the existing process route. For example, the alkylation on the benzene ring easily produces positional isomer due to the impacts from nitryl. The especial case is that the 2-oxo-indoline ring after ring formation must be protected by acylation to achieve the smooth condensation reaction in which methylene is produced. The removal of acylation Pg will affect the functional groups of the other amide in the product, leading to the increased side reactions to reduce yield and quality.

In view of the flaws in the existing process, the development of economical and environmentally friendly preparation technique with simple process can greatly promote the industrial production of the API and improve its economic and social benefits, and in this technique, the seeking for the synthetic route without protection and with deprotection is especially important.

SUMMARY OF THE INVENTION

The present invention aims to provide a preparation method of Nintedanib. The preparation method has an easily obtained raw material and a simple process, is economical and environmentally friendly, and is suitable for industrial production.

To achieve the above object of the present invention, the following technical scheme is mainly adopted in the present invention: a preparation method of Nintedanib (I),

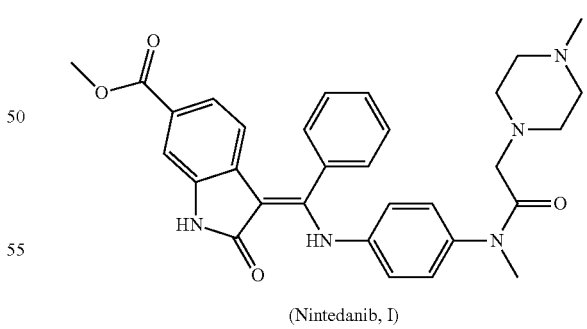

(Nintedanib, I)

comprising the following steps: carrying out a condensation reaction on 4-(R acetate-2-yl)-3-nitrobenzoate (II) and trimethyl orthobenzoate to obtain (E)-4-[(2-methoxybenzylidene) R acetate-2-yl]-3-nitrobenzoate (III); carrying out a substitution reaction on the compound (EI) and N-(4-aminophenyl)-N-methyl-2-(4-methyl piperazine-1-yl) acetamide (IV) under the action of an acid-binding agent to generate (Z)-4-{[2-(N-methyl-2-(4-methyl piperazine-1-yl)

acetamido-aniline) benzylidene] R acetate-2-yl}-3-nitrobenzoate (V); and sequentially carrying out reduction reactions and cyc-lization reactions on the compound (V) to prepare the Nintedanib (I). Wherein, R in said 4-(R acetate-2-yl)-3-nitrobenzoate (II) is methyl, ethyl, aliphatic group with 1 to 10 carbon atoms, phenyl or benzyl, but methyl or ethyl for the optimization case.

The molar ratio of raw material 4-(R acetate-2-yl)-3-nitrobenzoate (II) and trimethyl orthobenzoate for said condensation reaction is 1:1~10, but 1:2~6 for the optimization case.

The solvent used in said condensation reaction is acetic anhydride.

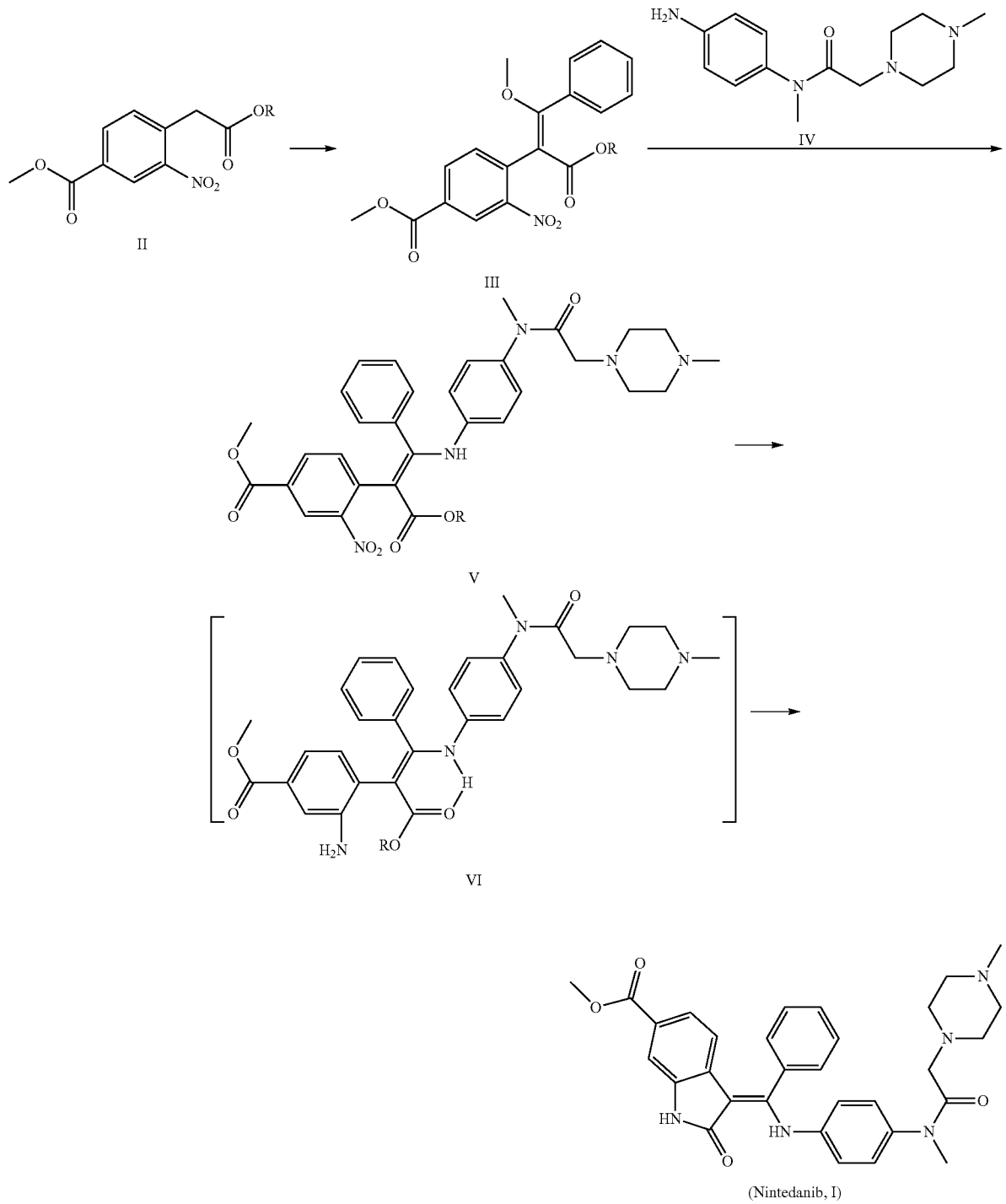

(Nintedanib, I)

In addition, the following attached technical scheme is included in the present invention:

The temperature for said condensation reaction is 110~130° C.

The molar ratio of raw material (E)-4-[(2-methoxybenzylidene) R acetate-2-yl]-3-nitrobenzoate (III) and N-(4-aminophenyl)-N-methyl-2-(4-methyl piperazine-1-yl) acetamide (IV) for said substitution reaction is 1:0.5-1.5, but 1:1~1.2 for the optimization case.

The solvents used in said substitution reaction are N,N-dimethylformamide, N,N-dimethylacetamide, dioxane, dimethylsulfoxide, methylbenzene or dimethylbenzen, but N,N-dimethylformamide or dioxane for the optimization case.

The acid-binding agents used in said substitution reaction are triethylamine, pyridine, 4-methylmorpholine, diisopropylethylamine, 4-dimethylaminopyridine, potassium carbonate, lithium carbonate or potassium tert-butoxide, but pyridine, lithium carbonate or diisopropylethylamine for the optimization case.

The temperature for said substitution reaction is 50~100° C., but 80~90° C. for the optimization case.

The reductive agents used in said reduction reaction are iron powder, tin powder, zinc powder, aluminite powder, rongalite, hydrazine hydrate, stannous chloride, sodium sulphide or hydrogen, but iron powder, zinc powder or hydrogen for the optimization case.

The acid catalysts added for said metal reduction are hydrochloric acid, phosphoric acid, acetic acid or acetic anhydride, but anhydride for the optimization case.

If the hydrogen is used as the reductive agent in said reduction reaction, the catalysts used are palladium carbon, platinum carbon, palladium hydroxide or raney nickel, but palladium carbon or platinum carbon for the optimization case.

The solvents used in said catalytic hydrogenation are methyl alcohol, ethyl alcohol, propyl alcohol or isopropyl alcohol, but ethyl alcohol or isopropyl alcohol for the optimization case.

The temperature for said cyclization reaction is 50~150° C., but 110~120° C. for the optimization case.

The solvents used in said cyclization reaction are benzene, methylbenzene, dimethylbenzene, acetic acid, acetic anhydride or dioxane, but methylbenzene, acetic acid or acetic anhydride for the optimization case.

The product from said reduction reaction needs no post-processing, and can be directly used for the cyclization reaction.

Compared with the existing technology, the preparation method of Nintedanib (I) in the present invention has an easily obtained raw material and a simple process and is economical and environmentally friendly, which is beneficial to the industrial production of the API consequently to promote the development of economy and technology.

DETAILED DESCRIPTION

The unrestricted detailed description for the technical scheme of the present invention is further given, based on the following several preferred embodiments. The preparation method of raw material 4-(R acetate-2-yl)-3-nitrobenzoate (II) and N-(4-aminophenyl)-N-methyl-2-(4-methyl piperazine-1-yl) acetamide (IV) can be referred to *J. Med. Chem*, Pages 4466-4480, Vol. 52, 2009 and *Chinese Journal of Pharmaceuticals*, Pages 726-729, Vol. 43, Issue 9, 2012 where the preparation method of the same compounds are introduced.

Embodiment 1

Add 4-(methyl acetate-2-yl)-3-nitrobenzoate (II) (2.53 g, 10 mmol), trimethyl orthobenzoate (9.10 g, 50 mmol) and 30 mL acetic anhydride into the reaction bottle, and get it heated to reflux status with the reaction of 6~8 hours. After that, the end of the reaction is found by TLC detection. When it cools down to the room temperature, there is separated solid. The crude generated product is recrystallized through normal hexane and ethyl acetate (1:1, V/V) and dried in the air to get 2.65 g off-white solid (E)-4-[(2-methoxybenzylidene) methyl acetate-2-yl]-3-nitrobenzoate (III) with 71.4% yield.

Melting point is 172-474° C. and mass spectrum (EI) is m/z 372 (M+H).

Embodiment 2

Add 4-(benzyl acetate-2-yl)-3-nitrobenzoate (II) (3.29 g, 10 mmol), trimethyl orthobenzoate (5.46 g, 30 mmol) and 40 mL acetic anhydride into the reaction bottle, and get it heated to reflux status with the reaction of 8 hours. After that, the end of the reaction is found by TLC detection. When it cools down to the room temperature, there is separated solid. The crude generated product is recrystallized through normal hexane and ethyl acetate (1:2, V/V) and dried in the air to get 3.35 g off-white solid (E)-4-[(2-methoxybenzylidene) benzyl acetate-2-yl]-3-nitrobenzoate (Ill) with 74.9% yield. Melting point is 205-209° C. and mass spectrum (EI) is m/z 448 (M+H).

Embodiment 3

Add (E)-4-[(2-methoxybenzylidene) methyl acetate-2-yl]-3-nitrobenzoate (III) (3.71 g, 10 mmol), N-(4-aminophenyl)-N-methyl-2-(4-methyl piperazine-1-yl) acetamide (IV) (2.88 g, 11 mmol) and 50 mL N,N-dimethylformamide into the reaction bottle and get it heated to 80~85° C., and then stir it with the reaction of 2 hours. When it cools down to the room temperature, the acid-binding agent pyridine (5 mL) is added with the stirring of 2 hours at the room temperature. Pour the reaction liquid into 150 mL water, and produce the separated solid. Said separated solid is filtered, and the crude product from filtration is recrystallized through ethyl alcohol to get 4.32 g yellow solid (Z)-4-{[2-(N-methyl-2-(4-methyl piperazine-1-yl) acetamido-aniline) benzylidene] methyl acetate-2-yl}-3-nitrobenzoate (V) with 71.9% yield. Melting point is 185~188° C. and mass spectrum (EI) is m/z 602 (M+H).

Embodiment 4

Add (E)-4-[(2-methoxybenzylidene) benzyl acetate-2-yl]-3-nitrobenzoate (III) (4.47 g, 10 mmol), N-(4-aminophenyl)-N-methyl-2-(4-methyl piperazine-1-yl) acetamide (IV) (2.88 g, 11 mmol) and 50 mL dioxane into the reaction bottle and get it heated to 80~85° C., and then stir it with the reaction of 2.5 hours. When it cools down to the room temperature, the acid-binding agent lithium carbonate (1.1 g) is added with the stirring of 3 hours at the room temperature. Pour the reaction liquid into 150 mL water, and produce the separated solid. Said separated solid is filtered, and the crude product from filtration is recrystallized through methyl alcohol to get 4.93 g light yellow solid (Z)-4-{[2-(N-methyl-2-(4-methyl piperazine-1-yl) acetamido-aniline) benzylidene] benzyl acetate-2-yl}-3-nitrobenzoate (V) with 73.9% yield. Melting point is 222~224° C. and mass spectrum (EI) is m/z 678 (M+H).

Embodiment 5

Add (Z)-4-{[2-(N-methyl-2-(4-methyl piperazine-1-yl) acetamido-aniline) benzylidene] methyl acetate-2-yl}-3-nitrobenzoate (V) (3.0 g, 5 mmol), 10% palladium carbon (0.3 g, 10% w/w) and 25 mL isopropyl alcohol into the hydrogenation reactor, and based on the hydrogenation operating procedures, the following actions are taken: add hydrogen at the room temperature and under the pressure of 5-8 Kg/cm$^2$; then stir it with the reaction of 4 hours until no hydrogen is consumed. After filtration, the catalyst palladium carbon is recovered, the filtrate undergoing a condensation process through reducing the pressure, and then the residue is dissolved through methylbenzene. Under the increased temperature of 115~120° C., the reaction lasts 5 hours. After that, the end of the reaction is found by HPLC detection. Methylbenzene is recovered through reducing the pressure, and the residue is recrystallized through methyl alcohol to get 2.37 g yellow solid Nintedanib (I) with 87.9% yield. Melting point is 241-243° C. and mass spectrum (EI) is: m/z 540 (M+H), $^1$H NMR (DMSO d$_6$): 2.27 (s, 3H), 2.43 (111, 8H), 2.78 (s, 2H), 3.15 (s, 3H), 3.82 (s, 3H), 5.97 (d, J=8.3 Hz, 1H), 6.77 (d, J=8.7 Hz, 1H), 6.96 (d, J=8.6 Hz, 2H), 7.32-7.62 (m, 8H), 8.15 (s, 1H), 12.15 (s, 1H).

Embodiment 6

Add (Z)-4-{[2-(N-methyl-2-(4-methyl piperazine-1-yl) acetamido-aniline) benzylidene] benzyl acetate-2-yl}-3-nitrobenzoate (V) (3.4 g, 5 mmol) and 50 mL acetic anhydride into the reaction bottle, and iron powder (0.85 g, 15 mmol) is added in batches. The reaction lasts 4 hours at the increased temperature of 55~60° C. The following processes are cooling down and filtration, and then the filtrate is heated to 110~115° C. with the reaction of 5-6 hours. After that, the end of the reaction is found by HPLC detection. After condensation through reducing the pressure, the residue is recrystallized through methylbenzene to get 2.30 g yellow solid Nintedanib (I) with 85.3% yield. Melting point is 241~243° C. and mass spectrum (EI) is: m/z 540 (M+H), $^1$H NMR (DMSO d$_6$): 2.27 (s, 3H), 2.43 (m, 8H), 2.78 (s, 2H), 3.15 (s, 3H), 3.82 (s, 3H), 5.97 (d, J=8.3 Hz, 1H), 6.77 (d, J=8.7 Hz, 1H), 6.96 (d, J=8.6 Hz, 2H), 7.32-7.62 (m, 8H), 8.15 (s, 1H), 12.15 (s, 1H).

It should be pointed out that the embodiments mentioned above are used to only describe the technical designs and features of the present invention rather than limit the scope of protection of the present invention, because the aim is to make the persons familiar with this technology learn the contents of the present invention and then conduct implementation according to these embodiments. Any equivalent changes or modifications made according to the spirit and principles of the present invention will be included in the protection scope of the present invention.

The invention claimed is:

1. A preparation method of Nintedanib (I),

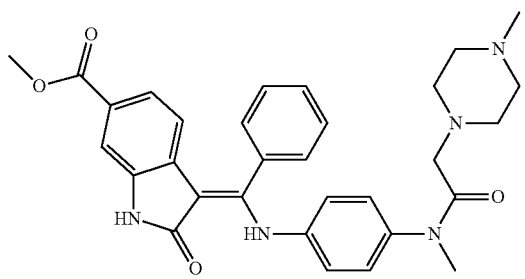

Nintedanib (I)

comprising the following steps as shown in the following scheme:

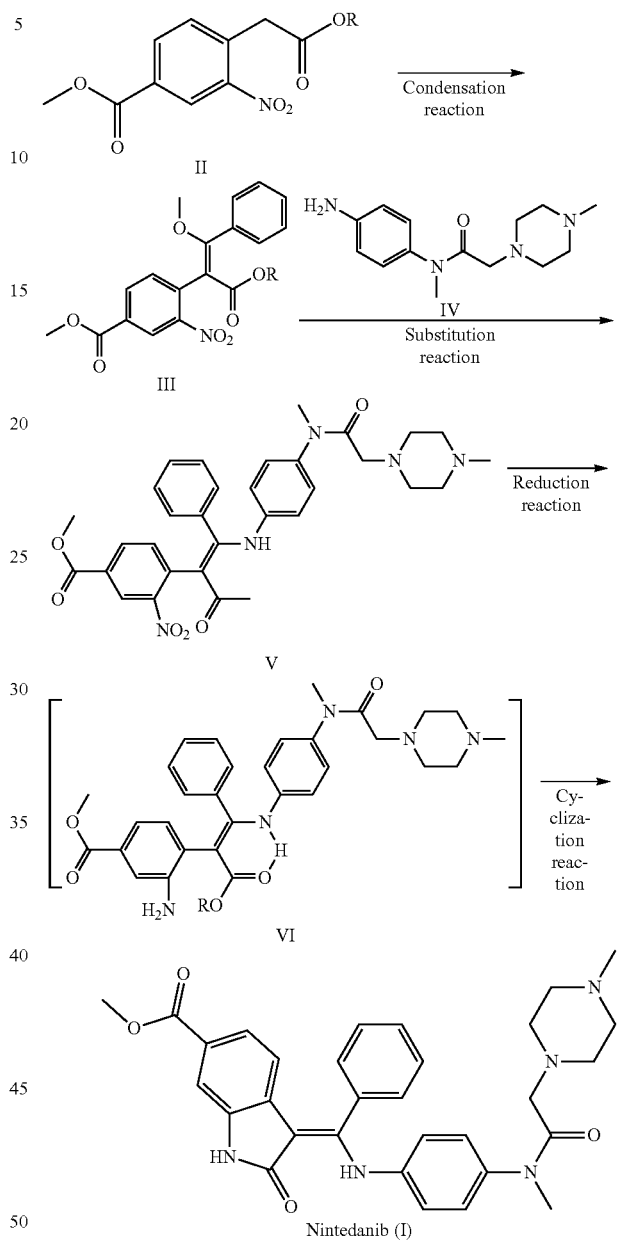

i) a condensation reaction-comprising condensing compound II and trimethyl orthobenzoate to provide compound III;
ii) a substitution reaction-comprising reacting compound III and compound IV in the presence of an acid-binding agent to provide compound V;
iii) a reduction reaction comprising reducing compound V to compound VI; and
iv) providing Nintedanib by a cyclization reaction comprising cyclizing compound VI; wherein R is selected from the group consisting of aliphatic group with 1 to 10 carbon atoms, phenyl, and benzyl.

2. The preparation method according to claim 1, wherein the molar ratio of compound II and trimethyl orthobenzoate is 1:1 to 1:10.

3. The preparation method according to claim 1, wherein the molar ratio of compound III and compound IV is 1:0.5 to 1:1.5.

4. The preparation method according to claim 1, wherein the acid-binding agent is selected from the group consisting of triethylamine, pyridine, 4-methylmorpholine, diisopropylethylamine, 4-dimethylaminopyridine, potassium carbonate, lithium carbonate, and potassium tert-butoxide.

5. The preparation method according to claim 1, wherein the temperature for said substitution reaction is 50° C. to 100° C.

6. The preparation method according to claim 1, wherein the reduction reaction is carried out in the presence of a reductive agent selected from the group consisting of iron powder, tin powder, zinc powder, aluminite powder, rongalite, hydrazine hydrate, stannous chloride, sodium sulphide, and hydrogen.

7. The preparation method according to claim 6, wherein hydrogen is used as the reductive agent in the presence of a catalyst selected from the group consisting of palladium carbon, platinum carbon, palladium hydroxide, and Raney nickel.

8. The preparation method according to claim 1, wherein the temperature for the cyclization reaction is 50° C. to 150° C.

9. The preparation method according to claim 1, wherein R is methyl or ethyl.

* * * * *